United States Patent
Karlen et al.

(12) 
(10) Patent No.: US 6,190,647 B1
(45) Date of Patent: *Feb. 20, 2001

(54) COMPOSITION FOR INCREASING THE STYLABILITY AND LUSTER OF THE HAIR

(75) Inventors: Thomas Karlen, Bern; Daniel Chambettaz, Ursen, both of (CH); Karin Steinbrecht, Ober-Ramstadt (DE)

(73) Assignee: Wella Aktiengesellschaft, Darmstadt (DE)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/113,476

(22) Filed: Jul. 10, 1998

(30) Foreign Application Priority Data

Jul. 31, 1997 (DE) ................................ 197 33 015
Sep. 16, 1997 (DE) ................................ 197 40 651

(51) Int. Cl.⁷ .............................. A61K 7/06; A61K 7/08; A61K 7/09
(52) U.S. Cl. .................. 424/70.2; 424/70.1; 424/70.11; 424/70.12; 424/70.16; 424/70.31; 132/202; 132/203
(58) Field of Search .................... 424/70.1, 70.2, 424/401, 70.11, 70.12, 70.16, 70.31; 514/880, 881; 132/202, 203

(56) References Cited

U.S. PATENT DOCUMENTS 5,278,269 * 1/1994 Mita et al. .
5,589,157 12/1996 Hatfield .
5,700,892 * 12/1997 Takiguchi et al. .
6,017,860 * 1/2000 Sajic et al. .

FOREIGN PATENT DOCUMENTS 0 590 604 A2   4/1994 (EP) .
0 623 336 A1  11/1994 (EP) .
91/11984   *  8/1991 (WO) .
94/26235      11/1994 (WO) .

* cited by examiner

*Primary Examiner*—Thurman K. Page
*Assistant Examiner*—Brian K. Seidleck
(74) *Attorney, Agent, or Firm*—Michael J. Striker

(57) ABSTRACT

The hair treatment composition for increasing the formability and luster of hair contains from 0.01 to 10 percent by weight of a copolymer formed from at least one ethylenic unsaturated monomer of the formula (I):

$$CH_2=CR^1R^2 \qquad (I),$$

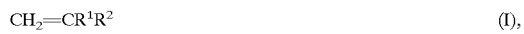

wherein $R^1$ is $A-(CH_2CH_2O)_x-R^3$ or COOH group and A is $C(=O)O$, $C(=O)NH$ or $CH_2O$, x is a number from 1 to 100, $R^3$ is a $C_8$- to $C_{30}$-alkyl group, $R^2$ is H, a $C_1$- to $C_{30}$-alkyl group or a $CH_2-R^1$ group, with the proviso that at least one of the groups, $R^1$ and $R^2$, contain the $A-(CH_2CH_2O)_x-R^3$ group; and from at least one ethylenic unsaturated monomer of the formula (II):

$$CH_2=CR^4COOR^5 \qquad (II),$$

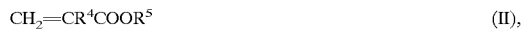

wherein $R^4$ and $R^5$ are, independently of each other, H or an alkyl group with 1 to 30 carbon atoms; from 0.01 to 50 percent by weight of a polyethylene glycol with a molecular weight over 500 g/mol and from 0.01 to 20 percent by weight of a nonionic surfactant having an HLB-value under 20.

13 Claims, No Drawings

US 6,190,647 B1

COMPOSITION FOR INCREASING THE STYLABILITY AND LUSTER OF THE HAIR

BACKGROUND OF THE INVENTION

The subject matter of the present invention concerns a composition for increasing the stylability or shapability and luster of the hair, which contains a special homopolymer or copolymer, a polyethylene glycol and a non-ionic surfactant.

For some time research efforts in the hair care composition field have had the goal of developing preparations for increasing the shapability or stylability and luster of hair. Currently pomades, creams, gels or waxes that have a high content of thickeners, emulsifiers or consistency-providing agents are used in order to guarantee the desired Theological properties and emulsion stability. It is disadvantageous however that this goal is attained with the currently used hair care composition only by use of high concentrations of the named materials, which, on the one hand, increases costs and, on the other hand, undesirably loads the hair.

SUMMARY OF THE INVENTION

It is an object of the present invention to provide a hair treatment composition that no longer has the above-described disadvantages.

According to the invention the hair treatment composition for increasing the formability and luster of hair has a content of:

(A) a homopolymer or copolymer formed from at least one ethylenic unsaturated monomer of the formula (I):

$$CH_2=CR^1R^2 \quad (I),$$

wherein $R^1$ is an $A-(CH_2CH_2O)_x-R^3$ or COOH group and A is a $C(=O)O$, $C(=O)NH$ or $CH_2O$ group, x is a number from 1 to 100, preferably from 10 to 50, $R^3$ is a $C_1$- to $C_{30}$-alkyl group, preferably a $C_8$- to $C_{30}$-alkyl group, $R^2$ is H, a $C_1$- to $C_{30}$-alkyl group or a $CH_2$-R group, with the proviso that at least one of the groups, $R^1$ and $R^2$, contain the $A-(CH_2CH_2O)_x-R^3$ group;

(B) a polyethylene glycol, and (C) a nonionic surfactant compound.

An unexpectedly strong, synergistic increase in viscosity and emulsifiability of the system occurs by a suitable combination of these three principal ingredients according to the invention, which cannot be obtained by the individual ingredients. The composition according to the invention is characterized by the fact that it forms stable emulsions with water-insoluble substances such as hydrocarbons or silicone oils. The rheological properties of the hair care compositions can be adjusted by variation of the content of the above-mentioned ingredients to provide the rheological properties of a pomade, cream, a wax or a gel.

Preferably component A is a copolymer which is formed from at least one ethylenic unsaturated monomer of the formula I and at least one ethylenic unsaturated monomer of the formula II

$$CH_2=C(R^4)COOR^5 \quad (II),$$

wherein $R^4$ and $R^5$ are, independently of each other, H or an alkyl group with 1 to 30, preferably 1 to 12, especially preferably from 1 to 4 carbon atoms.

Preferably A is $C(=O)O$ or $CH_2O$, R is H or methyl and the monomer of formula I is preferably an itaconic acid derivative. Similarly it is preferable when the monomer of formula II is acrylic acid, methacrylic acid or a $C_1$- to $C_4$-alkyl ester.

Suitable copolymers include, for example, acrylic or methacrylic acid/acrylic or methacrylic acid polyethoxy alkyl ester copolymers (INCI-name: Acrylates/steareth-20 methacrylate copolymer), such as those marketed under the trademark Acrylsol®-22, Acrylsol® ICS and Aculyn®-22 by the Rohm and Haas Co., U.S.A. or acrylic or methacrylic acid/polyethoxyalkylallyl ether copolymers (INCI-name: Steareth-10 allyl ether/acrylates copolymer), such as those sold under the tradename Salcare® SC 90 by Allied Colloids Co., Great Britain, or acrylic or methacrylic acid/itaconic acid polyethoxyalkyl ester copolymers (INCI-name: Acrylates/steareth-20 Itaconate Copolymer and Acrylates/Ceteth-20 Itaconate Copolymer), such as those sold under the tradenames Structure® 2001 and Structure® 3001 by National Starch, U.S.A.

The acrylic or methacrylic acid groups in the polymers included in the composition of the invention are neutralized preferably by organic or inorganic bases, especially by primary or secondary amines, e.g. by aminomethylpropanol (AMP). The polymer is contained in the hair treatment composition according to the invention in an amount of from 0.01 to 10, preferably in an amount of 0.05 to 3 percent by weight.

The polyethylene glycols contained in the composition according to the invention are fluid, waxy or wax-like or solid at room temperature. They generally have a molecular weight of over 500, preferably between 20,000 and 3,600,000 and are designated by the trademark Lipoxol® 1000 by Huls, by the trademark Pluracol® E 4000 by BASF, by the tradename Polyglycol by Hoechst, by the trademark Upi-wax® 20,000 by UPI Co. or by the type name Polyox® WSR-301 and Polyox® WSR-N-60 K by Union Carbide. The polyethylene glycol is present in the composition of the invention in an amount of from 0.01 to 50, preferably of 0.1 to 20 percent by weight.

The hair care compositions according to the invention also include a non-ionic surfactant as an additional important component. Preferably ethoxylated surfactant compounds containing between 1 and 1000 ethylene oxide units, most preferably 1 to 300, are present in the compositions. Fatty alcohol ethoxylates, fatty amine ethoxylates, fatty acid alkanolamide ethoxylates and fatty acid ester ethoxylates are particularly preferred. Examples of suitable fatty alcohol ethoxylates include ethoxylated lauryl-, tetradecyl-, cetyl-, oleyl- or stearyl alcohol, which can be used alone or in a mixture, as well as fatty alcohols of ethoxylate lanolin or ethoxylated lanolin. Also ethoxylated fatty alcohols, which are sold under the type name, Dehydol® by Henkel or under the type name Brij® of ICI surfactants, are suitable for the hair treatment composition according to the invention.

The fatty acid ester ethoxylates include, above all, diglyceride ethoxylate, such as that sold by ICI Surfactants under the trademark Arlatone® G; castor oil ethoxylated with 25 ethylene oxide units available under the INCI-name PEG-25 hydrogenated castor oil, which is sold by BASF under the trademark Cremophor® E1; castor oil ethoxylated with 35 ethylene oxide units available under the INCI name PEG-35 castor oil, which is sold by BASF under the trademark, Cremophor® RH 410; hydrogenated castor oil ethoxylated with 40 ethylene oxide units sold under the INCI name PEG-40, and the surfactant compounds sold under the name Rewoderm® LI, by Witco Co.

Furthermore the nonionic surfactant compounds that can be used for the cosmetic preparations according to the invention include known ethoxylated fatty acid sugar esters, especially ethoxylated sorbitan fatty acid ester, but also non-ethoxylated surfactants, such as the fatty acid sugar esters, which are sold under the trademarks Tween® and Arlacel® by the ICI Surfactants, the alkylpolyglycosides sold under the trademark Plantaren® or Plantacare by Henkel or by Seppic under the trademark Oramix®.

Generally any nonionic surfactant having an HLB-value under 20, preferably an HLB-value under 12 and especially preferably under 9, is suitable for the hair treatment compositions according to the invention.

Furthermore the composition according to the invention can contain other ingredients besides the above-mentioned three classes of substances. In the first place natural or synthetic film-forming, and thus hair fixing, polymers that are selected from the classes of anionic, cationic or amphoteric or nonionic polymers can be selected for inclusion in the compositions of the invention. These polymers usually are used in amounts of from 0.01 to 30 percent by weight, preferably in amounts of 0.5 to 10 percent by weight, but in the case of the cationic polymers the preferred concentration range is from 0.01 to 2 percent by weight.

The term "film-forming, hair-fixing polymer" means a polymer present in an amount of from 0.1 to 5% by weight in an aqueous, alcoholic or aqueous-alcoholic solution, that deposits a film on the hair and fixes the hair in this manner.

Suitable natural film-forming polymers with hair-fixing action include low molecular weight Chitosan having a molecular weight of 30,000 to 70,000 g/mol that is sold for example by Kyowa Oil & Fat Co., Japan. Different saccharide types can be used such as polysaccharides or mixtures of oligo-, mono- and disaccharides, which are sold for example under the trademark C-PUR® by Cerestar, Brussels. Also suitable natural polymers include Chinese Balsam resin and cellulose derivatives, e.g. hydroxypropyl cellulose with a molecular weight of 30,000 to 50,000 g/mol, that is sold for example under the trademark Nisso S1® by Lehmann & Voss, Hamburg. Shellac, such as sold under the tradename shellac MNP 210 by Fa. Pennig, Hamburg, is an additional suitable natural polymer. Shellac can be used in neutralized and unneutralized form.

Suitable synthetic film-forming anionic polymers include, e.g., crotonic acid/vinyl acetate copolymers, which for example are sold in the form of a 60% solution in isopropanol/water under the trademark Aristoflexs® by Hoechst. Additional suitable anionic polymers are, e.g. terpolymers of acrylic acid, ethyl acrylate and N-t-butylacrylamide, such as those marketed under the trademark Ultrahold® 8 and Ultrahold® strong of BASF.

The cationic polymers that can be used in the compositions of the invention include, e.g., polyvinyl pyrrolidone/dimethylaminoethylmethacrylate polymers, that are sold under the trademark Gafquat® 755 N of Gaf Co. New York. Additional cationic polymers include, for example, copolymers of polyvinyl pyrrolidone and imidazolimine methochloride, such as those sold under the trademark Luviquat® HM 550 by BASF; the terpolymer of dimethyldiallyl ammonium chloride, sodium acrylate and acrylamide sold under the trademark Merquat® Plus 3300 by Calgon Pittsburgh, PA, U.S.A.; the terpolymer of vinyl pyrrolidone, dimethylaminoethyl methacrylate and vinyl caprolactam that is marketed by ISP Co, U.S.A. under the trademark Gaffix® VC 713; the quaternary ammonium salt of hydroxyethyl cellulose and a trimethylammonium substituted epoxide sold under the trademark Polymer IR® by Amerchol, Edison, N.J., U.S.A.; the vinylpyrrolidone/methacrylamidopropyl trimethylammonium chloride copolymer sold under the trademark Gafquat® HS 100 of Gaf U.S.A. and diquaternary polydimethylsiloxane sold under the trademark Abil® Quat 3272 by Goldschmidt, Essen, Germany.

Suitable amphoteric polymers include, e.g., copolymers of octoylacrylamide, t-butylaminoethylmethacrylate and two or more monomers, comprising acrylic acid, methacrylic acid or their esters, such as are obtainable from National Starch, U.S.A under the trademark, Resyn® 28-4910 or Amphomer® LV-71.

Suitable synthetic nonionic film-forming, hair-fixing polymers include homopolymers of vinyl pyrrolidones, which for example are sold under the trademark, Luviskol® K of BASF or PVP-K of ISP, Wayne, N.J., U.S.A. and homopolymers of N-vinyl formamides, such as those sold under the tradename PVF of National Starch. Furthermore suitable synthetic film-forming, nonionic hair-fixing polymers include, e.g., copolymerizates of vinyl pyrrolidone and vinyl acetate that are sold under the trademark Luviskol® VA of BASF; terpolymers of vinyl pyrrolidone, vinyl acetate and vinyl propionate, that are sold, for example, under the trademark, Luviskol® VAP of BASF; polyacrylamides, such as those sold under the trademarks Akyponines® 191 of CHEM-Y, Emmerich or Sepigel® 305 of Seppic Co; polyvinyl alcohols, which are sold under the trademarks Elvanol® of Du Pont, or Vinol® 523/540 of Air Products and polyethyleneglycol/polypropylene glycol copolymers, that are sold under the trademark Ucon® of Union Carbide.

Furthermore polymers with a thickening action can be used if they are compatible with the remaining ingredients of the compositions according to the invention.

Homopolymers of acrylic acid with a molecular weight of from 2,000,000 to 6,000,000, such as those sold by BF Goodrich, Cleveland, Ohio under the trademark Carbopol® can be used as thickeners in the compositions according to the invention. As an additional thickener acrylic acid homopolymers with a molecular weight of 4,000,000, such as those sold by Goodrich under the trademark Carbopol® 940 can be used in the compositions according to the invention. Additional thickeners include for example acrylic acid homopolymers sold under the tradename Modarez V 600 PX by Protex, France or by Goodrich under the trademark Carbopol® ETD 2001; polymers of acrylic acid and acrylamide (sodium salts with a molecular weight of 2,000, 000 to 6,000,000) sold by Hoechst under the trademark Hostacerin® PN 73 and Sclerotium Gum sold by Alban Muller Montreal under the trademark Amigel®. The copolymers of acrylic acid or methacrylic acid, such as those sold by Goodrich under the trademark Carbopol® 1342 or Pemulen® TR1 are particularly preferred.

Water-soluble or water-insoluble silicone compounds can be used in the compositions of the invention in a concentration of from 0.01 to 50 percent by weight, preferably in a concentration of from 0.1 to 5 percent by weight. Volatile and nonvolatile cyclomethicones and dimethicones as well as dimethicone copolyols are especially preferred. Examples include polydimethylsiloxane (INCI: dimethicone), α-hydro-ω-hydroxypolyoxydimethylsilylene (INCI:dimethiconol), cyclic dimethylpolysiloxane (INCI: cyclomethicone), trimethyl-(octadecyloxy)silane (INCI: stearoxytrimethylsilane), dimethylsiloxane-glycol copolymer (INCI:dimethicone copolyol), dimethylsiloxane-aminoalkylsiloxane copolymer with hydroxy end groups (INCI: amodimethicone), monomethylpolysiloxane with lauryl side chains and polyoxyethylene and/or polyoxypropylene end chains (INCI: laurylmethicone copolyol), dimethylsiloxane glycol copolymer acetate (INCI: dimethiconecopolyol acetate) and dimethylsiloxane-aminoalkylsiloxane copolymer with trimethylsilyl end groups (INCI: trimethylsilyl-amodimethicone). Preferred silicone polymers include dimethicones that are sold, for example, under the tradename siloxane F-221 by Wacker, Munchen, Germany, or under the tradename Dow Corning Fluid 200/0.65 cs by Dow Corning Europe, Brussels; cyclomethicones that are sold for example under the tradenames Dow Corning 24 Fluid of Dow Corning Europe or Abil® K4 of Goldschmidt which for example is sold under the trademarks Silicone Fluid F-212 by Wacker or Unisil® SF-R of UPI.

The above-described names in parentheses correspond to the INCI nomenclature (International Cosmetic Ingredients), for naming cosmetic effective ingredients and auxiliary substances.

Mixtures of silicone polymers are also suitable, such as a mixture of dimethicone and dimethiconol that is sold, for example, under the tradename Dow Corning 1403 Fluid of Dow Corning, Europe.

Additional suitable silicone polymers include dimethicone copolyols that are sold under the tradename Surfactant 193 of Dow Corning Europe or Silwet® L of Union Carbide; amodimethicone which for example is sold under the tradename Sandoperm® FE by Sandoz or SM 2059 by General Electric U.S.A.; laurylmethicone copolyol that is sold under the tradename Dow Corning Q2-5200 by Dow Corning Europe; trimethylsilylamodimethicone that is sold under the tradename Dow Corning Q2-8220 by Dow Corning Europe or Silicone Fluid F-801 by Wacker; dimethicone copolyol acetate that is sold under the tradename silicone fluid VP or Belsil® DMC 6033 of Wacker and trimethyl-(octadecyloxy)-silane (INCI:stearoxytrimethylsilane), that is sold for example under the tradename Dow Corning 580 WAX by Dow Corning.

Water or alcohol-water mixtures can be added to the hair treatment compositions of the invention. Lower alcohols with 1 to 4 carbon atoms, such as ethanol and isopropanol, which are used for cosmetic purposes, can be contained in the compositions. Furthermore solvents or a mixture of solvents with a boiling point under 600° C. can be included in an amount of from 0.01 to 90 percent by weight, preferably from 2 to 50 percent by weight. Propylene glycols, such as glycerol, are especially suitable.

The composition according to the invention can also contain water-insoluble solvents or substances. For example, branched or unbranched hydrocarbons, such as pentane, hexane, isopentane and cyclic hydrocarbons, like cyclopentane and cyclohexane. Paraffins and isododecane are especially preferred.

Understandably the compositions according to the invention can contain additional cosmetic additive ingredients, such as non-fixing, nonionic polymers, non-fixing anionic polymers and non-fixing, natural polymers as well as combinations of those polymers in amounts of preferably from 0.01 to 50 percent by weight; perfume oils in an amount of preferably from 0.01 to 5 percent by weight; turbidity-inducing agents, such as ethylene glycol distearate, styrene-PVP copolymers, polystyrenes, in amounts of preferably from 0.01 to 5 percent by weight; wetting agents, surfactants or emulsifiers with or without wash activity from the classes of anionic, cationic, amphoteric surface-active substances, such as fatty alcohol sulfates, fatty alcohol ether sulfates, fatty acid alkanol amides, in an amount of preferably from 0.10 to 30 percent by weight; further moisturizing agents, dye substances, light protective agents, antioxidants, luster-giving ingredients and preservatives in an amount of preferably from 0.01 to 10 percent by weight. Furthermore the compositions according to the invention can also include a consistency- or body-giving substances used for example for creams. For example the compounds sold by Henkel under the tradename Lanette.

The surprising properties of the mixture according to the invention, as shown by the following examples, are especially clearly apparent from the viscosity measurements.

EXAMPLES

Viscosity measurements were performed with the rotation viscometer Haake VT-550 and viscosities were measured at 25° C. in mPas at 100/s. Mixtures of solutions 1, 2 and 3 with different nonionic surfactant compounds were prepared and the respective viscosity increase was determined. The results are reported in Tables I, II and III below. Solution 1: 3.0% by weight Acrylsol® 22 in water, neutralized with aminomethylpropanol to pH=7. Solution 2: 0.5% Polyox® WSR-301 in water/polypropylene glycol (9/1) Solution 3: polyglycol 200 0.5% water

TABLE I

Viscosity Increase due to Addition of Ethoxylated Surfactants to a Mixture of Acrysol® 22 with a High Molecular Weight Polyethylene Glycol

|  | V1 | V2 | V3 | V4 | V5 | V6 | V7 |
|---|---|---|---|---|---|---|---|
| Solution 1 | 50 | 48.75 | 48.75 | 48.75 | 48.75 | 48.75 | 48.75 |
| Solution 2 | 50 | 48.75 | 48.75 | 48.75 | 48.75 | 48.75 | 48.75 |
| Cremophor® RH 410 |  | 2.5 |  |  |  |  |  |
| Cremophor® EL |  |  | 2.5 |  |  |  |  |
| Dehydol® LS4 |  |  |  | 2.5 |  |  |  |
| Brij® 30 |  |  |  |  | 2.5 |  |  |
| Tween® 40 |  |  |  |  |  | 2.5 |  |
| Rewoderm® LI S 80 |  |  |  |  |  |  | 2.5 |
| Viscosity | 192 | 704 | 676 | 3255 | 3581 | 297 | 369 |

TABLE II

Viscosity Increase due to Addition of Ethoxylated Surfactants to a Mixture of Acrysol® 22 with a Low Molecular Weight Polyethylene Glycol

|  | V8 | V9 | V10 | V11 |
|---|---|---|---|---|
| Solution 1 | 50 | 48.75 | 48.75 | 48.75 |
| Solution 3 | 50 | 48.75 | 48.75 | 48.75 |
| Cremophor® RH 410 |  | 2.75 |  |  |
| Dehydol® LS |  |  | 2.75 |  |
| Rewoderm® LI S80 |  |  |  | 2.75 |
| Viscosity | <100 | 645 | 4572 | 329 |

TABLE III

Viscosity Increase due to Addition of Non-Ethoxylated Surfactants to a Mixture of Acrysol® 22 with a High Molecular Weight Polyethylene Glycol

|  | V12 | V13 |
|---|---|---|
| Solution 1 | 50 | 48.75 |
| Solution 2 | 50 | 48.75 |
| Plantacare® 818 UP |  | 2.75 |
| Viscosity | <192 | 1132 |

TABLE IV

Viscosity Increase due to Addition of Non-Ethoxylated Surfactants to a Mixture of Acrysol ® 22 with a Low Molecular Weight Polyethylene Glycol

|  | V12 | V13 |
|---|---|---|
| Solution 1 | 50 | 48.75 |
| Solution 2 | 50 | 48.75 |
| Plantacare ® 818 UP |  | 2.75 |
| Viscosity | <100 | 1132 |

The extreme and unexpected viscosity increase shown in the tables makes the mixture according to the invention suitable for making the following exemplary compositions of the invention.

EXAMPLE 1

Gel with Strong Fixing Action and Non-ionic Polymer

| 92.6 g | 2% Acrylsol ® 22 in water, with base adjusted to pH = 7 |
| 5.0 g | Luviskol ® K80 |
| 0.4 g | Polyox ® WSR-301 |
| 2.0 g | Cremophor ® RH 410 |
| 100.00 g | |

EXAMPLE 2

Gel with Strong Fixing Action and Amphoteric Polymer

| 92.3 g | 1.5% Acrylsol ® 22 in water, with base adjusted to pH = 7 |
| 5.0 g | Amphomer ®, neutralized with AMP |
| 0.7 g | Polyox ® WSR N-10 |
| 2.0 g | Cremophor ® RH 455 |
| 100.00 g | |

EXAMPLE 3

Gel with Strong Fixing Action and Anionic Polymer

| 92.4 g | 1.5% Acrylsol ® ICS-1 in water, with base adjusted to pH = 7 |
| 5.0 g | Luviset ® CAP, (copolymer of vinyl acetate, crotonic acid and vinylpropionic acid) |
| 0.6 g | Polyox ® WSR N-80 |
| 2.0 g | Cremophor ® EL |
| 100.00 g | |

EXAMPLE 4

Gel with strong Fixing Action and Non-ionic and Cationic Polymer

| 92.6 g | 1.5% Structure ® 2001 in water, with base adjusted to pH = 7 |
| 4.9 g | Luviskol ® VA 64 |
| 0.1 g | Gafquat ® 755 N |
| 0.4 g | Polyox ® WSR N-3000 |
| 2.0 g | Dehydol ® LS 4 |
| 100.00 g | |

EXAMPLE 5

Gel with Fixing Action and Protection from the Sun

| 92.2 g | 1.5% Acrysol ® 22 in water, with base adjusted to pH = 7 |
| 5.0 g | Luviskol ® VA 64 |
| 0.5 g | Uvinul ® P25 (p-aminobenzoic acid with 25 mol ethylene glycol) |
| 0.3 g | Polyox ® WSR-205 |
| 2.0 g | Dehydol ® LS 4 |
| 100.00 g | |

EXAMPLE 6

Gel with Moisturizing Effect

| 82.8 g | 1% Acrysol ® 22 in water, with base adjusted to pH = 7 |
| 5.0 g | Luviskol ® K 90 |
| 2.0 g | Brij ® 30 |
| 0.2 g | Polyox ® WSR N-60 K |
| 10.0 g | Glycerol |
| 100.00 g | |

EXAMPLE 7

Quick-drying Gel with Ethanol

| 61.0 g | 2.5% Salcare ® SC90 in water, with base adjusted to pH = 7 |
| 5.0 g | Luviskol ® K80 |
| 2.0 g | polyglycol 3000 |
| 2.0 g | Tween ® 40 |
| 30.0 g | ethanol |
| 100.00 g | |

EXAMPLE 8

Gel with Gentle Fixing Action and Silicone Oil as Luster-Giving Agent

| | |
|---|---|
| 83.8 g | 1.5% Structure ® 3001 in water, with base adjusted to pH = 7 |
| 3.0 g | silicone oil AK 500 |
| 0.2 g | Polyox ® WSR-301 |
| 3.0 g | Cremophor ® RH 410 |
| 10.0 g | Glycerol |
| 100.00 g | |

EXAMPLE 9

Pomade with Gentle Fixing Action

| | |
|---|---|
| 77.8 g | 1% Salcare ® SC90 in water, with base adjusted to pH = 7 |
| 10.0 g | Castor Oil PEG 25 |
| 0.2 g | Polyglycol 35000 |
| 2.0 g | Rewoderm ® LI S 80 |
| 10.0 g | glycerol |
| 100.00 g | |

EXAMPLE 10

Pomade with Fixing Effect

| | |
|---|---|
| 69.8 g | 1% Acrysol ® ICS-I in water, with base adjusted to pH = 7 |
| 10.0 g | Castor Oil PEG 25 |
| 3.0 g | Luviskol ® K 60 |
| 5.2 g | Polyglycol 200 |
| 2.0 g | Rewoderm ® LI S 80 |
| 10.0 g | Glycerol |
| 100.00 g | |

EXAMPLE 11

Pomade with Gentle Fixing Action and Long-lasting Luster

| | |
|---|---|
| 71.0 g | 1% Structure ® 2001 in water, with base adjusted to pH = 7 |
| 3.0 g | Kamol ® ID(isododecane) |
| 10.0 g | Castor Oil PEG 25 |
| 1.0 g | PEG-14000 |
| 2.0 g | Emulgin ® L(PPG-1-PEG-9-Lauryl glycol ether) |
| 10.0 g | Glycerol |
| 3.0 g | Dow Corning Q2-1403 |
| 100.00 g | |

EXAMPLE 12

Shaping and Luster-giving Cream

| | |
|---|---|
| 77.8 g | 1% Structure ® 3001 in water, with base adjusted to pH = 7 |
| 10.0 g | Paraffinium perliquidum |
| 0.2 g | Polyox ® WSR-301 |
| 2.0 g | Cremophor ® RH 410 |
| 10.0 g | Glycerol |
| 100.00 g | |

EXAMPLE 13

Shaping and Luster-giving Cream with Silicone Oil

| | |
|---|---|
| 77.2 g | 1% Acrylsol ® 22 in water, with base adjusted to pH = 7 |
| 5.0 g | Surfactant 193 |
| 5.8 g | Polyglycol 200 |
| 2.9 g | Cremophor ® EL |
| 10.0 g | Glycerol |
| 100.00 g | |

EXAMPLE 14

Fixing Cream without Loading

| | |
|---|---|
| 87.8 g | 1% Acrylsol ® 22 in water, with base adjusted to pH = 7 |
| 5.0 g | Luviskol ® K50 |
| 0.2 g | Polyox ® WSR-301 |
| 2.0 g | Cremophor ® RH 410 |
| 5.0 g | Kamol ® ID (isododecane) |
| 100.00 g | |

EXAMPLE 15

Shaping and Fixing Cream without Loading

| | |
|---|---|
| 76.8 g | 1% Acrylsol ® 22 in water, with base adjusted to pH = 7 |
| 10.0 g | Dow Corning Fluid 200/(0.65 mPas) |
| 0.2 g | Polyox ® WSR N-60K |
| 2.0 g | Dehydol ® LS 4 |
| 1.0 g | Cetiol ® HE |
| 100.00 g | |

EXAMPLE 16

Shaping and Luster-giving Cream with Sun Protecting Effect

| | |
|---|---|
| 86.3 g | 1% Salcare ® SC90 in water, with base adjusted to pH = 7 |
| 10.0 g | Dow Corning Fluid 200/(0.65 mPas) |
| 0.2 g | polygycol 1000 |
| 2.0 g | Dehydol ® LS 4 |
| 1.0 g | Cetiol ® HE |
| 0.5 g | Uvinul ® P25 (p-aminobenzoic acid with 25 mol ethylene glycol) |
| 100.00 g | |

EXAMPLE 17

Luster-giving Wax with Silicone Oil

| | |
|---|---|
| 71.4 g | 2.5% Acrylsol ® 22 in water, with base adjusted to pH = 7 |
| 3.0 g | Luviskol ® K 120 |
| 10.0 g | Abil ® K4 |
| 0.4 g | Polyox ® WSR-301 |
| 5.4 g | Cremophor ® RH 410 |
| 10.0 g | Glycerol |
| 100.00 g | |

EXAMPLE 18

Luster-giving Wax with Paraffin Oil

| | |
|---|---|
| 71.4 g | 2.5% Acrylsol ® 22 in water, with base adjusted to pH = 7 |
| 3.0 g | Luviskol ® K 120 |
| 10.0 g | Paraffin perliquidum |
| 0.4 q | Polyox ® WSR-301 |
| 5.0 g | Cremophor ® RH 410 |
| 10.0 g | Glycerol |
| 100.00 g | |

EXAMPLE 19

Styling Wax

| | |
|---|---|
| 74.8 g | 2% Acrylsol ® 22 in water, with base adjusted to pH = 7 |
| 3.0 g | Luviskol ® 120 |
| 10.0 g | Abil ® K4 |
| 0.2 g | Polyox ® WSR-301 |
| 2.0 g | Cremophor ® RH 410 |
| 10.0 g | Glycerol |
| 100.00 g | |

The disclosures of German Patent Applications 197 33 015.0 and 197 40 651.3 of Jul. 31, 1997 and Sep. 16, 1997 are hereby explicitly incorporated by reference. These German Patent Applications disclose the invention as described herein and claimed in the claims appended hereinbelow and are the basis for a claim of priority for the instant invention under 35 U.S.C. 119.

While the invention has been illustrated and described as embodied in a composition for increasing the stylability and luster of the hair, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

What is claimed is:

1. A hair treatment composition for increasing the formability and luster of hair containing:

from 0.01 to 10 percent by weight of a copolymer, said copolymer being formed from at least one ethylenic unsaturated monomer of the formula (I):

$$CH_2=CR^1R^2 \quad (I),$$

wherein $R^1$ is $A-(CH_2CH_2O)_x-R^3$ or COOH group and A is $C(=O)O$, $C(=O)NH$ or $CH_2O$, x is a number from 1 to 100, $R^3$ is a $C_8$- to $C_{30}$-alkyl group, $R^2$ is H, a $C_1$- to $C_{30}$-alkyl group or a $CH_2-R^1$ group, with the proviso that at least one of the groups, $R^1$ and $R^2$, contain the $A-(CH_2CH_2O)_x-R^3$ group; and from at least one ethylenic unsaturated monomer of the formula (II):

$$CH_2=CR^4COOR^5 \quad (II),$$

wherein $R^4$ and $R^5$ are, independently of each other, H or an alkyl group with 1 to 30 carbon atoms;

from 0.01 to 50 percent by weight of a polyethylene glycol having a molecular weight over 500 g/mol and from 0.01 to 20 percent by weight of a nonionic surfactant having an HLB-value under 20.

2. A hair treatment composition for increasing the formability and luster of hair containing:

from 0.01 to 10 percent by weight of a copolymer, said copolymer being formed from at least one ethylenic unsaturated monomer of the formula (I):

$$CH_2=CR^1R^2 \quad (I),$$

wherein $R^1$ is $A-(CH_2CH_2O)_x-R3$ or COOH group and A is $C(=O)O$, $C(=O)NH$ or $CH_2O$, x is a number from 1 to 100, R3 is a $C_8$- to $C_{30}$-alkyl group, $R^2$ is H, a $C_1$- to $C_{30}$-alkyl group or a $CH_2-R^1$ group, with the proviso that at least one of the groups, $R^1$ and $R^2$, contain the $A-(CH_2CH_2O)_x-R^3$ group; and from at least one ethylenic unsaturated monomer of the formula (II):

$$CH_2=CR^4COOR^5 \quad (II),$$

wherein $R^4$ and $R^5$ are, independently of each other, H or an alkyl group with 1 to 30 carbon atoms;

from 0.01 to 50 percent by weight of a polyethylene glycol;

from 0.01 to 20 percent by weight of a nonionic surfactant having an HLB-value under 20; and from 0.01 to 30 percent by weight of at least one active agent selected from the group consisting of natural hair-fixing polymers, synthetic anionic hair-fixing polymers, synthetic cationic hair-fixing polymers, synthetic amphoteric hair-fixing polymers, synthetic nonionic hair-fixing polymers, water-soluble silicone compounds, water-insoluble silicone compounds and hydrocarbons.

3. The composition as defined in claim 1 or 2, further comprising at least one member selected from the group consisting of water and alcohols with 1 to 4 carbon atoms.

4. The composition as defined in claim 1 or 2, further comprising at least one member selected from the group consisting of water, ethanol and isopropanol.

5. The composition as defined in claim 1 or 2, wherein said A is said $C(=O)O$ or said $CH_2O$ and said $R^2$ is said H or methyl.

6. The composition as defined in claim 1 or 2, wherein said copolymer is an acrylic or methacrylic acid/acrylic- or methacrylic acid polyethoxyalkyl ester copolymer, an acrylic- or methacrylic acid/polyethoxylalkylallyl ether copolymer or an acrylic- or methacrylic acid/itaconic acid polyethoxyalkyl ester copolymer.

7. The composition as defined in claim 1 or 2, wherein said copolymer has free carboxylic acid groups and said free carboxylic acid groups are present in neutralized form.

8. The composition as defined in claim 1 or 2, wherein said at least one ethylenic unsaturated monomer of the formula (II) is selected from the group consisting of acrylic acid, methacrylic acid, a $C_1$- to $C_4$-alkyl ester of said acrylic acid and a $C_1$- to $C_4$-alkyl ester of said methacrylic acid.

9. The composition as defined in claim 2, wherein said polyethylene glycol has a molecular weight over 500 g/mol.

10. The composition as defined in claim 1, wherein said molecular weight is from 20,000 to 3,600,000.

11. The composition as defined in claim 1 or 2, wherein said nonionic surfactant contains a fatty alcohol ethoxylate, a fatty amine ethoxylate, a fatty acid alkanolamide ethoxylate or a fatty acid ester ethoxylate.

12. The composition as defined in claim 1, further comprising from 0.01 to 30 percent by weight of a natural or synthetic, anionic, cationic, amphoteric or nonionic hair-fixing polymer.

13. The composition as defined in claim 1, further comprising from 0.01 to 30 percent by weight of a water-soluble or water-insoluble silicone compound.

* * * * *